United States Patent [19]
Goulait et al.

[11] Patent Number: 5,527,305
[45] Date of Patent: Jun. 18, 1996

[54] DISPOSABLE ABSORBENT ARTICLES HAVING A PAPER REINFORCED TAPE LANDING

[75] Inventors: David J. K. Goulait; Sheila S. Rodriguez; David W. Cabell, all of Cincinnati, Ohio

[73] Assignee: The Proctor & Gamble Company, Cincinnati, Ohio

[21] Appl. No.: 435,554

[22] Filed: May 5, 1995

Related U.S. Application Data

[63] Continuation of Ser. No. 125,711, Sep. 23, 1993, abandoned.

[51] Int. Cl.$^6$ ........................................... A61F 13/15
[52] U.S. Cl. ................. 604/390; 604/385.1; 604/387; 604/389
[58] Field of Search ............................ 604/358, 385.1, 604/382, 389–391

[56] References Cited

U.S. PATENT DOCUMENTS

| | | | |
|---|---|---|---|
| 4,850,992 | 7/1989 | Amaral et al. | 604/385.1 |
| 5,147,347 | 9/1992 | Huang et al. | 604/389 |

FOREIGN PATENT DOCUMENTS

| | | | |
|---|---|---|---|
| 0286030A1 | 10/1988 | European Pat. Off. | |
| 4118859 | 8/1992 | Germany | 604/390 |
| WO93/07845 | 4/1993 | WIPO | |

OTHER PUBLICATIONS

Petranyi et al. *Repeatedly closable diaper* Translation of German Patent 4,118,859 pp. 1–11.

*Primary Examiner*—Randall L. Green
*Assistant Examiner*—Robert Clarke
*Attorney, Agent, or Firm*—Steven W. Miller; E. Kelly Linman; Jacobus C. Rasser

[57] ABSTRACT

A disposable absorbent article having an improved internal reinforcement strip comprising a paper (i.e., cellulosic) material. The disposable absorbent article has an adhesive tape fastening system preferably comprising tape tabs disposed adjacent each longitudinal edge and a landing member for refastenably adhering to the tape tabs. The landing member consists of a portion of the external surface of the backsheet. An internal reinforcement strip comprising a paper material is positioned so as to correspond with at least the landing zone. The reinforcement strip is joined to the internal surface of the backsheet. The use of paper for the material of the reinforcement strip provides a low cost yet effective reinforcement of the landing zone and an excellent substrate for printing of indicia that will aid in proper positioning of the absorbent article.

4 Claims, 2 Drawing Sheets

5,527,305

DISPOSABLE ABSORBENT ARTICLES HAVING A PAPER REINFORCED TAPE LANDING

This is a continuation of application Ser. No. 08/125,711, filed on Sep. 23, 1993 now abandoned.

FIELD OF THE INVENTION

The present invention relates to disposable absorbent articles such as diapers or adult incontinence briefs, and more particularly, to disposable absorbent articles having adhesive fastening tapes and a landing zone for the adhesive fastening tapes that is internally reinforced with a paper reinforcement strip.

BACKGROUND OF THE INVENTION

Disposable absorbent articles like baby diapers or adult incontinence briefs are well known in the art and commercially sold on a broad scale. Many of the commercially available diapers or briefs comprise an adhesive tape fastening system to secure the articles on a baby or an incontinent adult. The performance of the adhesive tape fastening system represents a key element for the functionality of such articles and therefore contributes to the commercial success of absorbent articles incorporating adhesive tape fastening systems.

Commercially available disposable absorbent articles generally comprise a liquid pervious topsheet, a liquid impervious backsheet, and an absorbent core placed between the topsheet and the backsheet.

The liquid impervious backsheet typically is a thin polyolefin film, almost always a polyethylene film. For economic, aesthetic and ecological reasons it is desirable to use films of a low caliper, for example, having an average nominal caliper of less than about 0.036 mm (1.4 mils).

The adhesive on the fastening tapes is selected such that the tapes will not fail in use. However, it is frequently desirable to unfasten the tapes to inspect the diaper for soiling for readjustment of the tapes. However, it is extremely difficult to formulate an adhesive for the fastening tapes that is sufficiently aggressive to prevent failure in use, yet allows peeling of the tape without tearing or stretching of the backsheet.

It is therefore a design objective for disposable absorbent articles to provide a reinforced landing area for the fastening tapes that allows use of an aggressive adhesive and yet at the same time allows unfastening of the tapes by peeling without stretching or tearing the backsheet.

For convenient reference, the surface of the backsheet facing the absorbent core of the absorbent article will be referred to as the internal surface of the backsheet. Similarly, the surface of the backsheet facing away from the absorbent core will be referred to as the external surface of the backsheet.

Numerous ways for reinforcing the landing zone of the backsheet have been proposed in the art.

U.S. Pat. No. 4,210,144, issued on Jul. 1, 1980 to Sarge III et al. proposes the use of a hot melt adhesive printed onto the backsheet in the landing zone for reinforcement of the landing zone. The hot melt adhesive may be applied as a continuous coating or as discrete lines or beads. The adhesive may be applied to the internal or external surface of the backsheet.

U.S. Pat. No. 4,296,750 issued to Woon et al. on Oct. 27, 1981 discloses a strip of adhesive applied to the internal surface of the backsheet in the landing zone.

U.S. Pat. No. 3,848,598 issued to Mesek on Nov. 19, 1974 discusses the reinforcement of disposable diapers having a closure system comprising either safety pins or adhesive tapes. The reinforcement materials in Mesek may be scrim or a strip of a polymer material having a high elastic modulus. The reinforcement material may be secured to either the internal or external surface of the backsheet, albeit that a "rough" reinforcement material is preferably secured to the internal surface of the backsheet.

European Patent Application 0 080 648A to Widlund published on Jun. 8, 1983 discloses the use of a smooth polymer film secured to the external surface of the backsheet. The polymer film is preferably made of polyester.

U.S. Pat. No. 5,024,672, issued Jun. 18, 1991 to Widlund discloses a similar reinforcement strip, however having an embossed surface. The reinforcement strip in Widlund is also placed on the external surface of the backsheet.

European Patent Application 0 287 767A to Koester published on Oct. 26, 1988 discloses a reinforcement strip secured to the internal surface of the backsheet. The reinforcement strip is made of a synthetic polymeric material and is adhered to the backsheet using a pressure sensitive adhesive.

U.S. Pat. No. B1 4,662,875 issued May 5, 1987 to Hirotsu & Robertson discloses a diaper having indicia printed on the backsheet for facilitating a symmetric application of the absorbent article. The indicia may be printed on a separate reinforcement strip which is secured to the internal surface or external surface of the backsheet.

The prior art in general relies on the use of expensive and stiff synthetic polymer materials, be it adhesive or polymer films, for use as a reinforcement member. The scrim material in Mesek appears to be an exception but scrim material is in any event too costly for use in disposable absorbent articles.

It is, therefore, an object of the present invention to provide a reinforced landing zone for the backsheet of a disposable absorbent article by utilizing a reinforcement member that is less expensive than a reinforcement member of synthetic polymer material.

It is a further object of this invention to provide a reinforcement member that is more resistant to heat, and therefore more suitable to be used with a hot melt adhesive than a reinforcement member made of a synthetic polymer material.

It is yet another object of the present invention to provide a reinforcement member that provides a suitable substrate for printing, and when printed provides better character definition for the indicia printed thereon than polyolefin materials.

SUMMARY OF THE INVENTION

The present invention relates to disposable absorbent articles having an improved internal reinforcement strip comprising a paper (i.e., cellulosic) material. The disposable absorbent article has an adhesive tape fastening system preferably comprising tape tabs disposed adjacent each longitudinal edge of said body portion in said first waist region, each tape tab having a fastening surface having an adhesive coated thereon; a landing member for refastenably adhering to said adhesive to form a bond during use of the absorbent article, the landing member consisting of a portion of the external surface of the backsheet in the second waist region of the absorbent article; and an internal reinforcement strip comprising a paper material positioned so as to correspond with at least said landing zone, the reinforcement strip being joined to the internal surface of the backsheet.

The use of paper for the material of the reinforcement strip provides a low cost yet effective reinforcement of the landing zone of the disposable absorbent article. Furthermore, paper provides an excellent substrate for printing of indicia that will aid in proper positioning of the absorbent article when fastening around a baby or incontinent adult. Furthermore, it has been found that customary amounts of an opacifier like titanium dioxide may be added to the backsheet material of the disposable absorbent article without adversely affecting the visibility of such indicia printed onto a strip of paper.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawing in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable"is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other disposable absorbent articles such as incontinent undergarments, diaper holders, feminine hygiene garments, and the like.

Figure 1:
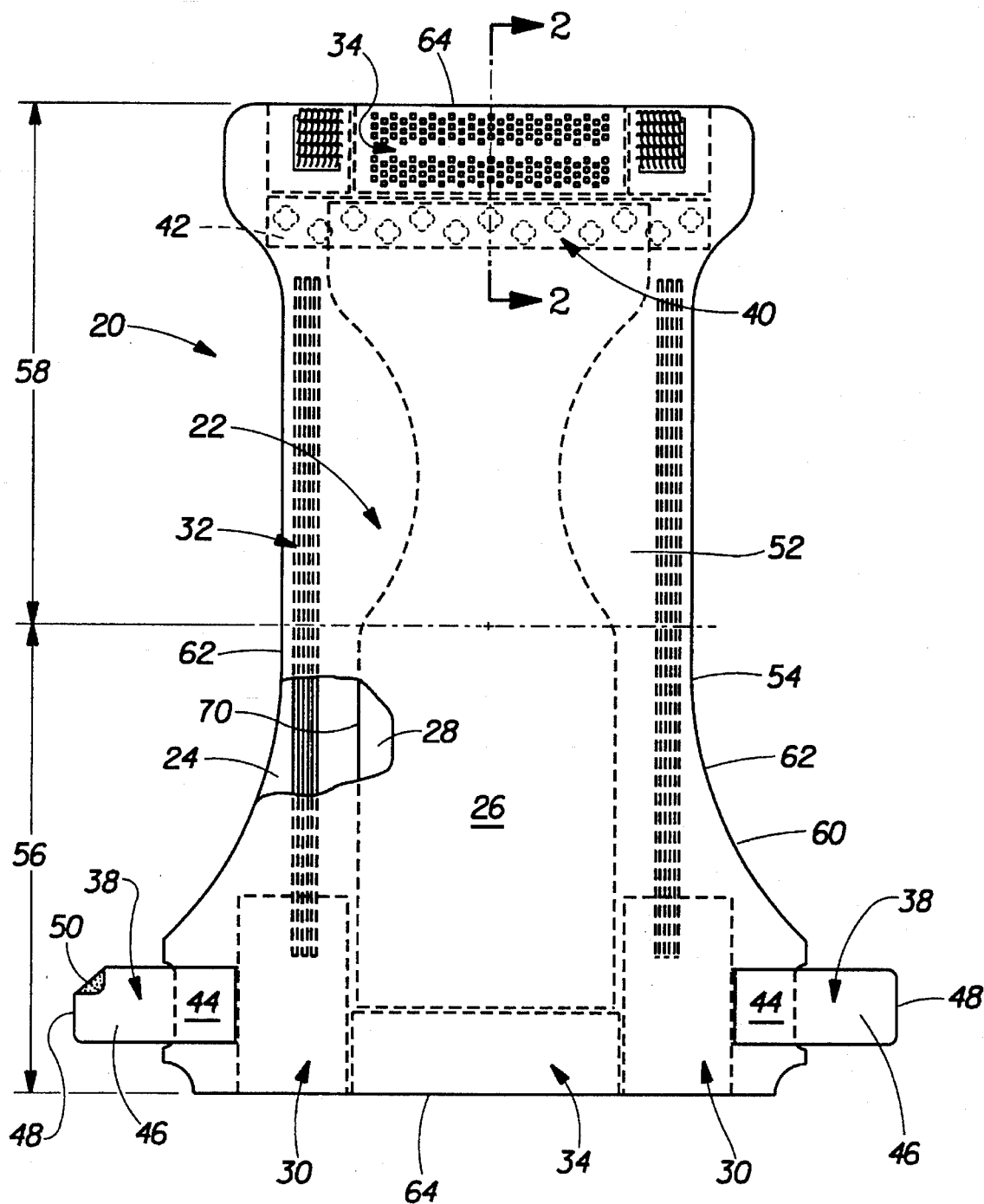
FIG. 1 is a plan view of a disposable absorbent article incorporating the adhesive fastening system of the present invention.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces away from the wearer, the outer surface 52, facing the viewer. As shown in FIG. 1, the diaper 20 preferably comprises (a) a body portion 22 comprising a liquid pervious topsheet 24, a liquid impervious backsheet 26 joined with the topsheet 24, and an absorbent core 28 positioned between the topsheet 24 and the backsheet 26; and (b) an adhesive tape fastening system. The adhesive tape fastening system comprises tape tabs 38, a landing member 40, and an internal reinforcement strip 42.

The body portion 22 of the diaper 20 is shown in FIG. 1 as comprising the main body (chassis) of the diaper 20. The body portion 22 comprises at least an absorbent core 28 and preferably an outer covering layer comprising the topsheet 24 and the backsheet 26. The body portion is shown in FIG. 1 to have an outer surface 52, an inner surface 54 opposed to the outer surface 52, a first waist region 56, a second waist region 58 opposed to the first waist region 56, and a periphery 60 which is defined by the outer edges of the diaper 20 in which the longitudinal edges are designated 62 and the end edges are designated 64. The inner surface 54 of the diaper 20 comprises that portion of the diaper 20 which is positioned adjacent to the wearer's body during use (i.e., the inner surface 54 generally is formed by at least a portion of the topsheet 24 and other components joined to the topsheet 24). The outer surface 52 comprises that portion of the diaper 20 which is positioned away from the wearer's body (i.e., the outer surface 52 generally is formed by at least a portion of the backsheet 26 and other components joined to the backsheet 26).

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 60 of the diaper 20. While the topsheet 24, the backsheet 26, and the absorbent core 28 may be assembled in a variety of well known configurations, preferred diaper configurations are described generally in U.S. Pat. No. 3,860,003 entitled "Contractable Side Portions For Disposable Diaper" issued to Kenneth B. Buell on Jan. 14, 1975 and U.S. Pat. No. 5,151,092 entitled "Absorbent Article With Dynamic Elastic Waist Feature Having A Predisposed Resilient Flexural Hinge" issued to Kenneth B. Buell, et al. on Sep. 29, 1992; each patent being incorporated herein by reference.

Figure 2:
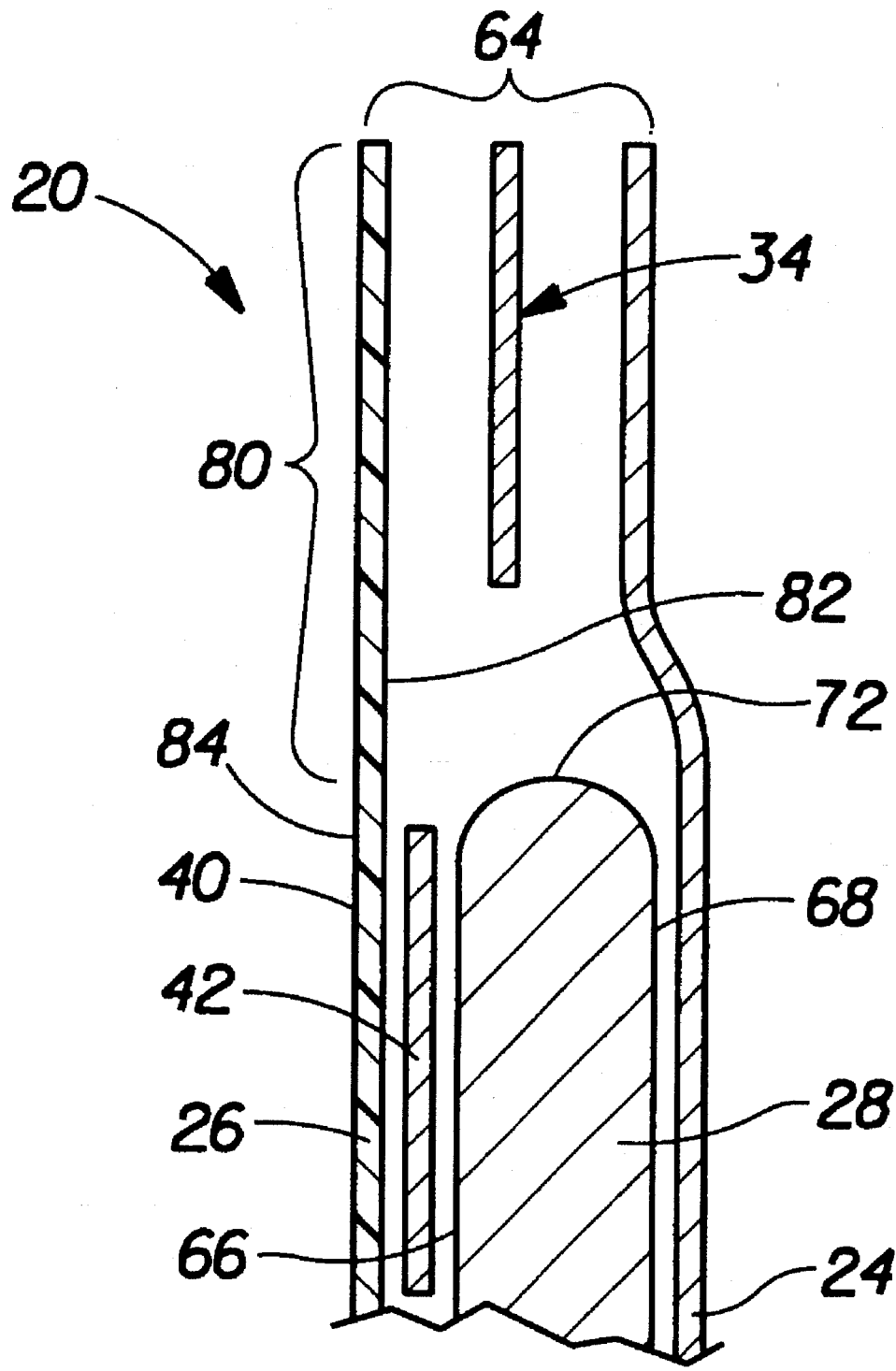
FIG. 2 is a cross section of the front waist portion of the disposable absorbent article taken along section line 2—2 of FIG. 1.

FIG. 2 is a fragmentary cross-sectional view of the diaper 20 taken along section line 2—2 of FIG. 1. The absorbent core 28 is generally shown in FIG. 2 and shows the waist edge 72 of the absorbent core 28. The topsheet 24 and the backsheet 26 encase the absorbent core 28 and extend longitudinally outwardly beyond the waist edge 72 of the absorbent core to form a waist flap 80 and the end edge 64. The internal reinforcement strip 42 is positioned adjacent the internal surface 82 of the backsheet between the backsheet and the absorbent core. The internal reinforcement strip 42 is joined to the internal surface 82 of the backsheet by strip attachment means (not shown) for joining the strip to the backsheet so as to reinforce the landing member.

The absorbent core 28 may be any absorbent means which is generally compressible, conformable, non-irritating to the wearer's skin, and capable of absorbing and retaining liquids such as urine and other certain body exudates. As shown in FIGS. 1 and 2, the absorbent core 28 has a garment surface 66, a body surface 68, side edges 70, and waist edges 72. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core should, however, be compatible with the design loading and the intended use of the diaper. Further, the size and absorbent capacity of the absorbent core 28 may be varied to accommodate wearers ranging from infants through adults. Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. A preferred embodiment of the absorbent core 28 has a dual layer construction comprising an acquisition/distribution layer preferably comprising chemically stiffened cellulosic fibers, and a storage core preferably comprising a mixture of fibers and absorbent gelling materials. An example of such an absorbent core is described generally in U.S. Pat. No. 4,935,022 entitled "Thin Absorbent Articles Containing Gelling Agent" issued to Lash on Jun. 19, 1990. Each of these patents are incorporated herein by reference.

The backsheet 26 is positioned adjacent the garment surface 66 of the absorbent core 28 and is preferably joined thereto in certain zones by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258 and HL-1347X. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 thus preferably comprises polymeric films such as thermoplastic films of polyethylene or polypropylene. Preferably, the backsheet is a thermoplastic film having a thickness of from about 0.012 mm (0.5 mil) to about 0.051 mm (2.0 mils). For economic, aesthetic, and ecological reasons, the backsheet 26 preferably has an average caliper of less than about 0.036 mm (1.4 mils), more preferably an average caliper of from about 0.020 mm (0.8 mil) to about 0.036 mm (1.4 mils), most preferably from about 0. 025 mm(1.0 mil) to about 0.030 mm (1.2 mil).

Preferably, the backsheet 26 is a flexible polyethylene film. As used herein, the term "polyethylene" film refers to films which are essentially made of polyethylene, however, it is understood that polyethylene film will contain a variety of additives to provide characteristics like opacity, strength, color, or any other desired characteristic that can be achieved through adding minor amounts of other substances than polyethylene into the films. The total amount of additives should be less than 45%, preferably less than 15%, by weight of film materials. Particularly, for opacity of the film, titanium dioxide is commonly used in a range of 2–6%, preferably 3.5–4.8%, by weight of the film. Exemplary films for use as the backsheet of the present invention are manufactured by Tredegar Industries, Inc. of Terre Haute, Ind. under the designation HTS-II. The backsheet 26 is preferably textured as described hereinafter to enhance the performance of the fastening system and to provide a more clothlike appearance. Further, the backsheet 26 may also permit vapors to escape from the absorbent core 28 while still preventing exudates from passing through the backsheet 26 by, for example, being supplied with microapertures as described, for example, in U.S. Pat. No. 4,681,793. The backsheet may also be biodegradable such as the film disclosed in WO 93/00116 "Disposable Absorbent Articles With Biodegradable Backsheets", Toms and Wnuk, published on Jan. 7, 1993, which is incorporated herein by reference.

The topsheet 24 is positioned adjacent the body surface 68 of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery 60 and are indirectly joined together by directly joining them to the absorbent core 28 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 28. There are a number of manufacturing techniques which may be used to manufacture the topsheet 24. For example, the topsheet 24 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The diaper 20 preferably further comprises elasticized leg cuffs 32 for providing improved containment of liquids and other body exudates. Each elasticized leg cuff may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. While each elasticized leg cuff 32 may be configured so as to be similar to any of the leg bands, side flaps, barrier cuffs, or elastic cuffs described above, it is preferred that each elasticized leg cuff 32 comprise the configuration shown in U.S. Pat. No. 4,695,278 comprising a barrier cuff and a gasketing cuff comprising one or more, preferably a plurality of, elastic members and a portion of the side flap.

The diaper 20 preferably further comprises an elastic waist feature 34 that provides improved fit and containment. The elastic waist feature 34 is that portion or zone of the diaper 20 which is intended to elastically expand and contract to dynamically fit the wearer's waist. The elastic waist feature 34 at least extends longitudinally outwardly from at least one of the waist edges 72 of the absorbent core 28 and generally forms at least a portion of the end edge 64 of the diaper 20. Disposable diapers are generally constructed so as to have two elastic waist features, one positioned in the first waist region and one positioned in the second waist region, although diapers can be constructed with a single elastic waist feature. Further, while the elastic waist feature or any of its constituent elements can comprise a separate element affixed to the diaper, the elastic waist feature is preferably constructed as an extension of other elements of the diaper such as the backsheet 26 or the topsheet 24, preferably both the backsheet 26 and the topsheet 24. The elasticized waist feature 34 may be constructed in a number of different configurations including those described in U.S. Pat. No. 4,515,595 issued to Kievit et al. on May 7, 1985 and the above-referenced U.S. Pat. No. 5,151,092; each of these patents being incorporated herein by reference.

In an especially preferred embodiment, the diaper also comprises elasticized side panels 30 disposed in the second waist region 58. (As used herein, the term "disposed" is used to mean that an element(s) of the diaper is formed (joined and positioned) in a particular place or position as a unitary structure with other elements of the diaper or as a separate element joined to another element of the diaper. ) The elasticized side panels 30 provide an elastically extensible feature that provides a more comfortable and contouring fit by initially conformably fitting the diaper to the wearer and sustaining this fit throughout the time of wear well past when the diaper has been loaded with exudates since the elasticized side panels allow the sides of the diaper to expand and contract. The elasticized side panels further provide more effective application of the diaper since even if the diaperer pulls one elasticized side panel farther than the other during application (asymmetrically), the diaper will "self-adjust" during wear. While the diaper 20 of the present invention preferably has the elasticized side panels 30 disposed in the second waist region 58; alternatively, the diaper may be provided with elasticized side panels disposed in the first waist region 56 or in both the first waist region 56 and the second waist region 58. While the elasticized side panels 30 may be constructed in a number of configurations, examples of diapers with elasticized side panels positioned in the ears (ear flaps) of the diaper are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and the hereinbefore referenced U.S. Pat. No. 5,151, 092; each of which are incorporated herein by reference. The preferred elasticized side panels comprise a zero strain laminate such as described in U.S. Pat. No. 5,151,092.

The diaper 20 is provided with an adhesive tape fastening system for forming a side closure on each side of the diaper 20. Thus, the diaper 20 is fitted to the wearer and the first waist region 56 and the second waist region 58 are maintained in an overlapping configuration when the diaper 20 is worn such that lateral tensions are maintained around the circumference of the diaper to maintain the diaper on the wearer.

In a preferred embodiment of the present invention as shown in FIG. 1, the adhesive tape fastening system comprises a pair of closure members, each preferably comprising a tape tab 38; a landing member 40 consisting of at least a portion of the external surface 84 of the backsheet 26, the tape tabs 38 being adhered to the landing member 40 in use; and an internal reinforcing strip 42 comprising a paper material joined to the internal surface 82 of the backsheet 26 at least coincident with the landing member 40.

The closure member is intended to provide a means for adhesively engaging the landing member so as to provide a secure bond or closure to secure the diaper on the wearer. Thus, the closure member preferably comprises an adhesive fastening means for adhesively engaging the landing member. The closure member also preferably comprises a means for positioning the fastening means adjacent the landing member so as to provide a bond. Thus, the closure members of the present invention preferably comprise either an inner fastening member or a tape tab, most preferably a tape tab.

An inner fastening member comprises a strip, patch, or layer of adhesive positioned on the body portion 22 of the diaper 20. Exemplary examples of inner fastening members are described in U.S. Pat. No. 4,699,622 issued to Toussant & Hasse on Oct. 13, 1987; U.S. Pat. No. 5,019,072 issued to Polski on May 28, 1991; and U.S. Pat. No. 4,850,988, issued to Aledo et al. on Jul. 25, 1989, each of which are incorporated herein by reference.

As shown in FIG. 1, each closure member most preferably comprises a tape tab 38. At least one tape tab is disposed adjacent each longitudinal edge 62 of the body portion 22 in the first waist region 56 of the diaper 20. (For large incontinent briefs, two or more tape tabs may be positioned on each longitudinal side such as is shown in U.S. Pat. No. 4,253,461; however, for simplicity purposes, FIG. 1 shows only one tape tab 38 on each side.) Each tape tab 38 has a fixed end 44 and a connective end 46. The fixed end 44 (i.e., that end of the tape tab 38 joined to the body portion 22 during manufacture) is permanently attached to the body portion 22. The term "permanently attached", as used herein, refers to an attachment which does not release under normal usage conditions of a disposable diaper 20. The connective end 46 is that end of the tape tab 38 that extends outwardly from the body portion 22 beyond the longitudinal edge 62 and that is grasped by the diaperer in securing the diaper on the wearer. The connective end 46 comprises a tape backing material onto which a layer of adhesive is coated.

In a preferred embodiment, each tape tab 38 preferably further comprises a release tape (not shown) joined to the topsheet 24. The release tape allows the connective end to be inwardly folded during manufacture to protect the adhesive on the tape tab 38 from contamination or delamination prior to use. (An alternative configuration for the tape tab is a Y-bond construction such as is shown and explained in detail in U.S. Pat. No. 3,848,594 entitled "Tape Fastening System For Disposable Diapers" which issued to Kenneth B. Buell on Nov. 19, 1974, and which patent is incorporated herein by reference.)

Optionally, the tape tab 38 can be provided with grip tabs at the distal edge 48 of the tape tab 38. Grip tabs may be formed, for example, by folding part of the fastening surface 50 at the outer edge of the connective end 46 onto itself. Grip tabs are preferably 2 mm to 8 mm, more preferably about 3 mm, wide. Grip tabs can also be provided by having the distal edge 48 not covered by adhesive. Additionally, the distal edge 48 of the tape tab 38 may be provided with rounded edges for additional user comfort.

Each tape tab 38 comprises a tape backing material which can be any of the tape backing materials well known in the art. For example, polyester films, polypropylene films, paper backings, or other materials which provide the required strength to be useful as part of a tape tab during use of a diaper, are suitable for use as the tape backing material. Particularly, tape backing materials of polypropylene film having a caliper of about 0.152 mm have been found to perform satisfactorily. The same materials used for the tape backing material can be used for the release tape. In order to perform its release function, the side of the release tape that is not attached to the topsheet 24 can be coated with a release agent, preferably with a silicone release coating which is well known in the art.

A layer of adhesive is coated onto the tape backing material to provide the adhesive fastening means for adhesively engaging the landing member. (As used herein, the term "coated" is not to be limited to any specific technique or method for applying the adhesive onto the tape backing material). The adhesive tape fastening system may use any suitable adhesive known in the art. The adhesive can, for example, be a hot melt adhesive which is coated onto the tape backing by any of the well known hot melt coating processes (e.g., by a slot coating process). Alternatively, the adhesive can be supplied in a solvent coating process. Preferably, the adhesive is an elastomeric pressure-sensitive adhesive. It is particularly preferred that such an adhesive material comprises a tackified rubber elastomer.

In accordance with the present invention, it has been found that tape tabs (tape backing material and adhesive) such as are manufactured by the Minnesota Mining and Manufacturing Company, St. Paul, Minn., under the designation KR 2045 with 8018 adhesive or KS 2048 with 0115 adhesive, have been found to provide satisfactory performance in the adhesive tape fastening systems of the present invention. Examples of suitable tape tabs are further described in U.S. patent application Ser. No. 07/782,707, entitled "Refastenable Adhesive Fastening Systems For Disposable Absorbent Articles" which was filed by Blaney and Priem-Chisholm on Oct. 25, 1991, and which is incorporated herein by reference.

The joining of the fixed end 44 to the body portion 22 can be provided by mechanical or preferably by adhesive means. In a preferred embodiment, the tape backing of the tape tab 38 is covered across its whole width with the same adhesive. This adhesive, thus, not only provides the fastening means at the connective end 46 but also the attachment to permanently adhere the tape tab 38 to the backsheet 26 at the fixed end 44.

The adhesive tape fastening system further comprises a landing member 40. The landing member 40 provides a means for refastenably adhering itself and the adhesive disposed on the connective end 46 of the tape tab together to form a secure but refastenable bond so as to provide a side closure for the diaper. The landing member 40 may be disposed anywhere on the external surface 84 of the backsheet so long as it engages the tape tab 38. Typically, the landing member 40 is disposed in the second waist region 58. The landing member 40 consists of at least a portion of the external surface 84 of the backsheet 26.

The landing member 40, the backsheet 26, is preferably manufactured so as to provide a surface that will optimize the adherence, release, and refastenability of the tape tab 38. For both strong adhesion of the adhesive to the landing member and good bond security, the external surface 84 of the backsheet must be receptive to the adhesive at low application pressures. Typically, it has been found that a "smooth" surface enhances bond security because the adhesive "wets" more of the surface. However, embossed surfaces are generally considered more aesthetically pleasing for their matte appearance at a sacrifice to bond security since the entire area is not wetted by the adhesive. It has been discovered, however, that there is an optimum surface roughness for the external surface 84 of the backsheet. The external surface 84 of the backsheet preferably has certain surface characteristics that are believed to enhance the bond security of the adhesive fastening system. The external surface preferably have an average surface plane variation of less than about 1.2 times of the nominal average thickness (calculated caliper) of the backsheet. That is, the total caliper of the backsheet (the caliper taking into account the surface texture of the film) is preferably no greater than about 20% more than the nominal average thickness (initial caliper) of the film. The surface roughness of the backsheet, when measured with a Perthometer M4P profilometer apparatus such as sold by Feinpruef Corporation of Blue Ash, Ohio, has an average peak-valley height of less than about 12 microns, more preferably less than about 10 microns, and most preferably less than about 8 microns; and a maximum peak-valley height of less than about 15 microns, more preferably less than about 12 microns, most preferably less than about 10 microns.

In a preferred embodiment, the external surface 84 of the backsheet can have a texture surface roughness provided in a structured pattern or in a random pattern. In general, texturing of thermoplastic films is conducted by passing the film between a nip of a steel roll and a rubber roll. The steel roll contains the pattern such as, for example, square, round, random or other shapes as considered desirable for the particular usage of the thermoplastic film. The thermoplastic film is drawn into the nip between the two rolls which are pressed against each other. The depth of the texturing depends on the pattern provided on the steel roll. Depending on the thermoplastic film material, the steps of preheating of the thermoplastic film and cooling after the embossing can be added to the process. The external surface of the backsheet was generally designated to be that surface embossed by the steel roll. A more detailed description of texturing processes and apparatuses can be found in U.S. Pat. Nos. 4,436,520, 4,595,021, 4,546,029, 4,376,147 or WO 88/07336. However, according to the present invention, texturing of the thermoplastic film is provided by using a process in which, for example, a smooth non-patterned steel roll and a rubber roll are used in a similar way as described above. In this case, the surface textured by the rubber roll is used as the external surface of the backsheet. Preferably, the steel roll has a flat, sand blasted surface. The texturing of the external surface of the backsheet results from the rubber roll.

The internal reinforcement strip 42 reinforces the landing member 40 (i.e., the backsheet 26) so as to allow the tape tab 38 to be peeled from the landing member 40 without deforming or tearing the backsheet 26, thus permitting refastenability and secure repositioning of the tape tab 38 as required. As shown in FIG. 1 and FIG. 2, the internal surface 82 of the backsheet is reinforced by joining the internal reinforcement strip 42 to it. Thus, the laminate of the backsheet 26 and the internal reinforcement strip 42 resists stretching and tearing and results in improved tensile strength rendering the adhesive bond between the tape tab and the landing member peelable and refastenable.

The term internal reinforcement "strip" should be non-limiting in that the internal reinforcement "member" can be any size, shape, or thickness. For example, the internal reinforcement strip could be a relatively large area patch or patches of material secured to the inner surface of the backsheet, could be a layer of material attached to the entire internal surface of the backsheet, or could be one or more small patches secured to the internal surface. Preferably, the internal reinforcing strip 42 is a relatively narrow piece of paper having a generally rectangular shape that is a sufficient size to provide enough area corresponding to at least the predetermined surface area of the landing member on the external surface of the backsheet.

The internal reinforcement strip 42 is "joined" to the internal surface 82 of the backsheet by any appropriate means such as adhesive, ultrasonic bonding, dynamic mechanical bonding, or other suitable attachment means. Preferably, the internal reinforcing strip is adhesively joined to the internal surface 82.

The internal reinforcing strip 42 comprises a paper material. As used herein, the term "paper" is used herein to denote a layer made of chemically processed cellulosic fiber. The layer of cellulosic fibers may be processed into a number of conventional paper type layers including tissue or conventional paper. A paper internal reinforcement strip has several advantages over conventional polyolefinic materials used for internal reinforcement strips. A paper strip does not need to be treated (such as corona discharge treated) to enhance glue adhesion, allows higher adhesive application temperatures since the paper will not typically melt at the temperatures of hot melt adhesive applied to the paper, is more environmentally friendly in that paper will be biodegradable or compostable, is easier to process than typical polyolefinic films since it allows broader processing parameters, allows better definition of printing on the surface of the strip for indicia to allow taping, is more compatible with the absorbent core, and is lower in cost. Further, a paper internal reinforcing strip provides the reinforcing and strength enhancement properties with higher tensile strengths at much lower weights. Thus, the paper reinforcing strip provides enhanced refastenability for the adhesive fastening system.

In a preferred embodiment of the present invention, the paper internal reinforcement strip has certain defined physical properties to give an adhesive tape fastening system providing improved fastenability and refastenability. Preferably, the paper internal reinforcement strip has a basis weight of from about 10 to about 50 pounds per 3,000 square feet, more preferably from about 15 to about 30 pounds per 3,000 square feet. This basis weight range offers the internal reinforcement strip enough fiber and strength for good reinforcement. The caliper of the paper internal reinforcement strip is preferably between about 10 and about 25 mils. The total tensile strength needed for sufficient strength for both the finished product and processing needs of the paper internal reinforcement strip is about 700 to 18,000 g/in., with a machine direction (MD) tensile strength of about 500 to about 13,000 g/in and a cross-machine direction (CD) tensile strength of about 200 to about 5,000 g/in. For processing considerations, the paper material should exhibit both MD and CD stretch. The MD stretch should be between about 1% to about 20% with the CD stretch being from about 2% to about 10% at peak load. Since the paper internal reinforcement strip is likely to be in contact with the absorbent core and would be subject to wetted by urine or other body exudates, it is preferable that the paper internal reinforcement strip exhibit enough wet strength capability to sustain its reinforcement under wet loading conditions. Further, to provide a paper material on a high speed basis it is preferred that the paper material exhibit low porosity characteristics in the range of from about 0 to about 20 cubic feet of air per meter.

EXAMPLE 1

A diaper is formed comprising a polyethylene backsheet such as manufactured by Tredegar under the name HTS-II. The fastening tapes comprise a backing material and an adhesive such as is marketed by 3M under the name KR 2045 with an 8018 adhesive applied thereto. The internal reinforcement strip comprises a material supplied by 3M under the designation XPO-1074. The internal reinforcement strip is secured to the internal surface of the backsheet by an adhesive coated onto the entire surface of the internal reinforcement strip. The adhesive is marketed by Fuller under the tradename HL1347X. The internal reinforcement strip has a MD tensile strength of 12,500 g/in., a CD tensile strength of 4,100 g/in., a basis weight of 30 lbs. per 3,000 square feet, a tear strength of 75 grams, an MD stretch of 13% and CD stretch of 7.4%. The internal reinforcement strip is effective so that repeated refastening of the fastening tape to the landing member of the backsheet does not pucker, rip, or destroy the backsheet.

EXAMPLE 2

A disposable diaper is formed with the same characteristics as in Example 1 except that the fastening tapes are those manufactured by 3M under the designation KS 2048 with a 0115 adhesive material. The internal reinforcement strip comprises a 15 lb. paper such as manufactured by Tufco. The internal reinforcement strip has an MD tensile strength of 4,700 g/in., a CD tensile strength of 2,100 g/in., a basis weight of 16 lbs. per 3,000 square feet, a wet tensile strength of about 18–22 grams, an MD stretch of 1.8%, and a CD stretch of 2.4%. The internal reinforcement strip is effective so that repeated refastening of the fastening tape to the landing member of the backsheet does not pucker, rip, or destroy the backsheet.

EXAMPLE 3

A disposable diaper is formed similar to that in Example 2. The internal reinforcement strip comprises a 30 lbs. paper newsprint such as available from Robert Wolf Company of Freemont, Ohio. The internal reinforcement strip has an MD tensile strength of 6,500 g/in., a CD tensile strength of 2,700 g/in., a basis weight of 30 lbs. per 3,000 square feet, an MD stretch of 1.6%, and a CD stretch of 2.5%. The internal reinforcement strip is effective so that repeated refastening of the fastening tape to the landing member of the backsheet does not pucker, rip, or destroy the backsheet.

The diaper 20 is preferably applied to a wearer by positioning one of the waist regions, preferably the second waist region 58, under the wearer's back and drawing the remainder of the diaper between the wearer's legs so that the other waist region, preferably the first waist region 56, is positioned across the front of the wearer. The tape tabs 38 of the fastening system are then released from the release portion. The diaperer then wraps the elasticized side panel 30 around the wearer, while still grasping the connective end 46. The elasticized side panels will typically be extended and tensioned during this operation so as to conform to the size and shape of the wearer. The adhesive on the fastening surface 50 of the connective end 46 is secured to the landing member 40, the external surface 84 of the backsheet, that is reinforced by the internal reinforcement strip 42, to effect a side closure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
a body portion having a first waist region, a second waist region, longitudinal edges, and end edges, said body portion comprising a liquid pervious topsheet, a liquid impervious backsheet joined to said topsheet, and an absorbent core disposed between said topsheet and said backsheet, said backsheet having an internal surface positioned adjacent said absorbent core and an external surface opposed to said internal surface; and an adhesive tape fastening system comprising:
  a) a tape tab disposed adjacent each longitudinal edge of said body portion in said first waist region, each of said tape tabs having a fixed end and a connective end having a fastening surface, said fixed end being joined to said body portion, said connective end extending laterally outward from said longitudinal edge of said body portion, and said fastening surface being coated with an adhesive; and
  b) a landing member for refastenably adhering to said adhesive to form a bond during use of the absorbent article, said landing member consisting of at least a portion of said external surface of said backsheet in said second waist region; and
  c) an internal reinforcement strip coincident with at least said landing member, said internal reinforcement strip being joined to said internal surface of said backsheet and comprising a paper material having a basis weight of between about 15 lbs. per 3,000 square feet and about 30 lbs. per 3,000 square feet, a total tensile strength of between about 700 g/in and about 18,000 g/in and a cross machine direction tensile strength of between about 200 g/in and about 5,000 g/in.

2. The absorbent article of claim 1 wherein said internal reinforcement strip has an MD stretch of from about 12% to about 20%, and a CD stretch of from about 4% to about 12%.

3. The absorbent article of claim 2 wherein said external surface of said backsheet has a surface roughness having a Mean Leveling Depth of between about 3 microns and about 8 microns.

4. The absorbent article of claim 3 wherein said backsheet has an average nominal caliper of between about 0.020 mm and about 0.036 mm.

* * * * *